United States Patent
Temple

(10) Patent No.: US 9,795,286 B2
(45) Date of Patent: Oct. 24, 2017

(54) SCOPE WARMER WITH DISPOSABLE STERILE CASING

(71) Applicant: John Temple, Chelsea, MI (US)

(72) Inventor: John Temple, Chelsea, MI (US)

( * ) Notice: Subject to any disclaimer, the term of this patent is extended or adjusted under 35 U.S.C. 154(b) by 204 days.

(21) Appl. No.: 14/418,702

(22) PCT Filed: Oct. 2, 2014

(86) PCT No.: PCT/US2014/058792
§ 371 (c)(1),
(2) Date: Jan. 30, 2015

(87) PCT Pub. No.: WO2015/051098
PCT Pub. Date: Apr. 9, 2015

(65) Prior Publication Data
US 2016/0022128 A1 Jan. 28, 2016

Related U.S. Application Data

(60) Provisional application No. 61/886,396, filed on Oct. 3, 2013.

(51) Int. Cl.
*A61B 1/06* (2006.01)
*A61B 1/12* (2006.01)
(Continued)

(52) U.S. Cl.
CPC .......... *A61B 1/127* (2013.01); *A61B 1/00034* (2013.01); *A61B 1/00096* (2013.01);
(Continued)

(58) Field of Classification Search
CPC ..... A61B 1/05; A61B 1/0008; A61B 1/00105; A61B 1/0011; A61B 1/0676; A61B 1/127; A61B 1/00034; A61B 1/00131; A61B 1/00135; A61B 1/00142; A61B 1/00144; A61B 1/00147; A61B 1/128; A61B 1/00151; A61B 1/00154; A61B 1/12; A61B 1/169; G02B 23/2476
(Continued)

(56) References Cited

U.S. PATENT DOCUMENTS

| 1,414,494 A | * | 5/1922 | Arntfield | A47J 27/004 |
| | | | | 219/415 |
| 6,204,485 B1 | * | 3/2001 | Williams | A45D 44/00 |
| | | | | 219/429 |

(Continued)

*Primary Examiner* — Ryan Henderson
*Assistant Examiner* — Pamela F Wu
(74) *Attorney, Agent, or Firm* — John G. Posa; Belzer PC

(57) ABSTRACT

A laparoscope/endoscope warmer includes a rechargeable heater with an inexpensive, disposable casing so that the expensive portions of the system can be reused. An elongated heater has an outer wall, a closed end and an open end into a cavity having an inner wall. A heating element such as a heating coil is disposed between the inner and outer walls of the heater. A rechargeable battery within the heater powers the heating element. The heater fits into a charging base operative to recharge the rechargeable battery through cooperating electrical contacts or an inductive coupling. The sterile casing includes an inner sleeve that fits into the cavity of the heater unit, providing a receptacle to receive and warm the rod of an endoscope or laparoscope.

11 Claims, 3 Drawing Sheets

(51) Int. Cl.
*A61B 1/00* (2006.01)
*A61B 1/313* (2006.01)

(52) U.S. Cl.
CPC ...... *A61B 1/00103* (2013.01); *A61B 1/00131* (2013.01); *A61B 1/00135* (2013.01); *A61B 1/128* (2013.01); *A61B 1/3132* (2013.01)

(58) Field of Classification Search
USPC ..................... 600/114, 121–125, 186, 169
See application file for complete search history.

(56) References Cited

U.S. PATENT DOCUMENTS

| | | | |
|---|---|---|---|
| 7,311,660 B2* | 12/2007 | Gomez | A61B 1/127 126/263.04 |
| 7,952,322 B2* | 5/2011 | Partovi | H01F 5/003 320/108 |
| 7,999,511 B2 | 8/2011 | Umetsu | |
| 8,251,895 B2 | 8/2012 | Seeh et al. | |
| 2002/0022762 A1 | 2/2002 | Beane et al. | |
| 2005/0234301 A1* | 10/2005 | Gomez | A61B 1/127 600/169 |
| 2014/0069606 A1* | 3/2014 | Lee | A61J 9/001 165/63 |

* cited by examiner

SCOPE WARMER WITH DISPOSABLE STERILE CASING

FIELD OF THE INVENTION

This invention relates generally to laparoscope/endoscope warmers and, in particular, to such a warmer with a low-cost, disposable casing enabling the more expensive heater unit to be reused.

BACKGROUND OF THE INVENTION

When using endoscopes or laparoscopes, it is important that they are warmed to human body temperature or the objective optics will fog up. For this reason, there are several "scope warmers" on the market, including 'passive' devices that use an exothermic reaction, and active systems that use electrical heaters.

One of the electrical units, offered by New Wave Surgical of Coral Springs, Fla., is called the Defogging Heated Endoscopic Lens Protector. The tip of the laparoscope is inserted into a fist-sized, battery operated "anti-fog warmer" and white light balancer. The unit has a very short battery life, and it is discarded after use. Another option is offered by Mediflex of Islandia, N.Y. This design provides a plug-in heater with a 15-meter cord which is also disposed of after surgery. Both of these solutions are expensive and not 'environmentally friendly' due to the waste generated.

Due to the fact that rechargeable batteries cannot tolerate the heat of an autoclave (270° F.), and because batteries are not environmentally friendly, an electrically powered alternative design remains an outstanding need.

SUMMARY OF THE INVENTION

This invention improves upon existing electrically powered endoscope/laparoscope (i.e., "scope") warmers by providing a heater unit that operates in conjunction with an inexpensive, disposable sterile casing enabling the more expensive portions of the system (i.e., the heater, batteries, electrical controls) to be reused.

The heater unit has an open end into a cavity. A heating element such as a heating coil is disposed within the unit to heat the cavity. The sterile disposable casing fits over the heater, and includes an elongated inner sleeve that fits into the cavity of the heater. The inner sleeve in turn provides a receptacle configured to receive the rod portion of an endoscope or laparoscope to be warmed by the heater. In the preferred embodiments the casing includes a closure to entirely contain the heating unit.

Although non-rechargeable batteries may be used, the preferred embodiment uses a rechargeable battery (or batteries) within the heater unit to power the heating element. A charging base may be provided for recharging the heater unit. The heater unit and the charging base may either include a plurality of cooperating electrical contacts or an inductive coupling to recharge the batter(ies).

DETAILED DESCRIPTION OF THE INVENTION

This invention resides in a battery operated scope warmer. However, to avoid costly disposables and environmentally unfriendly waste present in current offerings, inexpensive disposable sterile casings are provided so that the heater unit can be reused.

Figure 1:
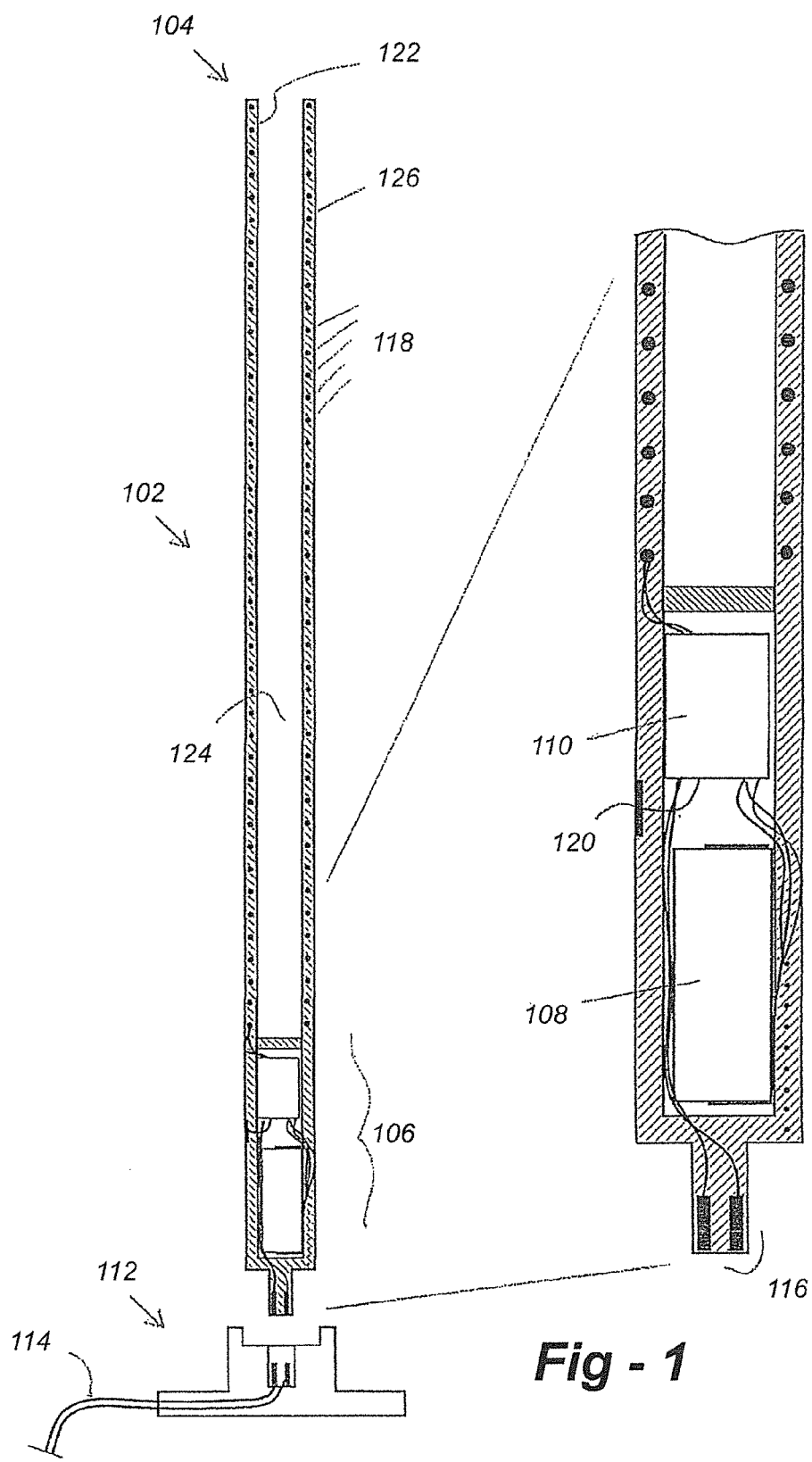
FIG. 1 is a simplified drawing in partial cross section illustrating a heater unit according to the invention.

The heater, shown generally at 102 in FIG. 1, is an enclosed, elongated unit having an open distal end 104 and a proximal end 106 including a rechargeable battery 108 and temperature controller 110. The heater fits into a base unit 112 interconnected to a power source such as AC mains through wires 114. The base unit and heater unit may have cooperating contacts 116, as shown, for recharging purposes, or an inductive charging system (not shown) may alternatively be used.

Battery 108 is operatively connected to temperature controller 110 which, in turn, is connected to heating coil 118. A touch switch 120 may be used to activate the coil upon removal from the base unit, or a sealed pushbutton may alternatively be used. The housing of the heater may be constructed from durable plastic with the various components moulded into the unit. In all embodiments, the inner wall 122 of the heater cavity 124 may be thinner than the outer wall 126 to improve heat transfer to the scope as described below.

Figures 2, 3:
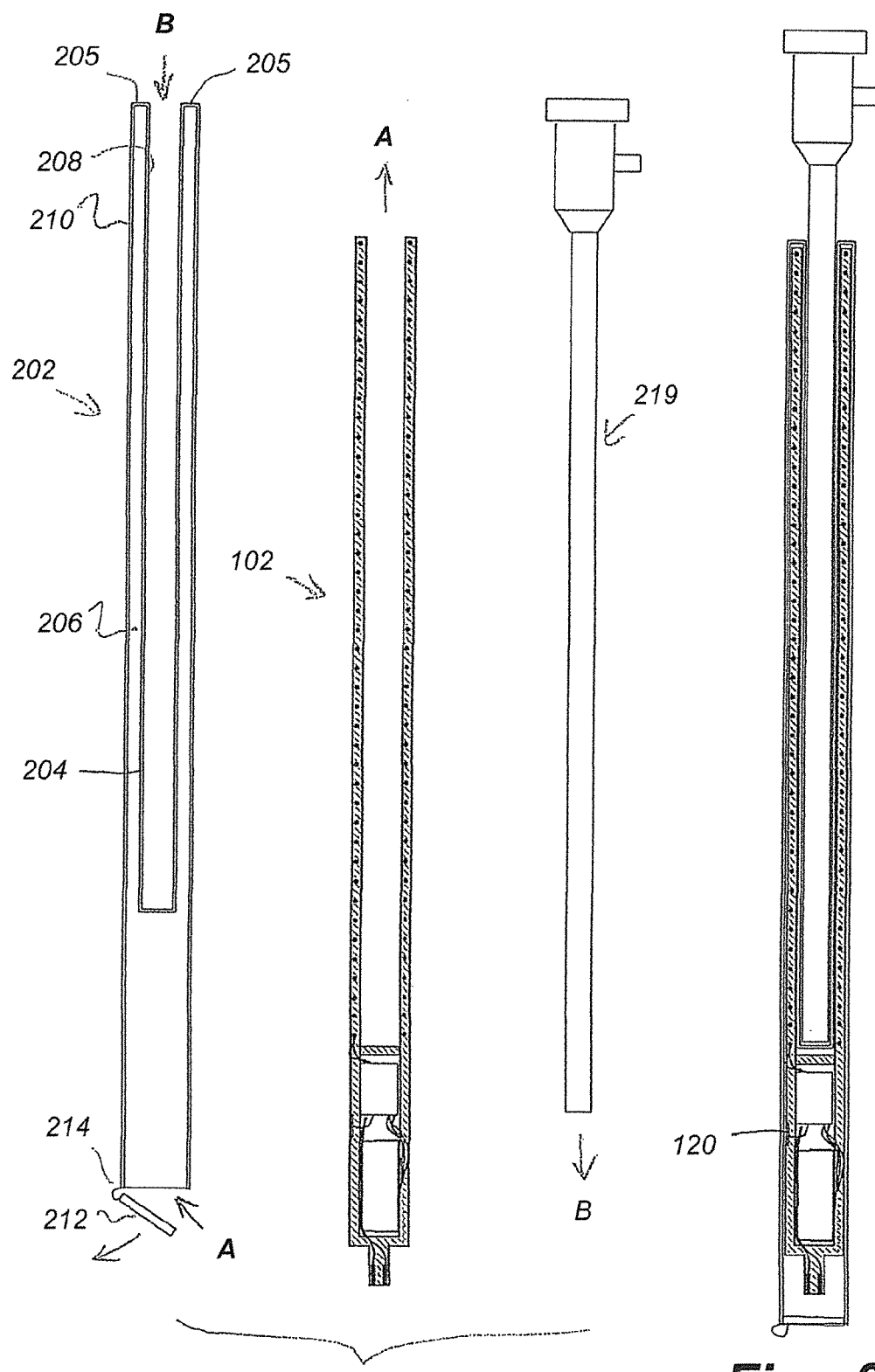
FIG. 2 shows the way in which the heater unit is received within a sterilized, disposable casing, and the way in which a scope is received by the inner sleeve of the casing.
FIG. 3 illustrates how the heater unit, casing and scope are nested during use.

FIG. 2 shows the way in which the heater unit 102 is received within a sterilized, disposable casing 202, and the way in which a scope 219 is received by an inner sleeve 204 of the casing. The casing is made from any suitable inexpensive material, including sterilisable plastics. The inner sleeve 204 of the casing is preferably a rigid or semi-rigid cylinder with a closed distal end, though a flexible or semi-flexible structure is also possible.

In the embodiment of FIG. 2, the inner sleeve 204 of the casing is connected to an outer sleeve 210 through a peripheral rim 205. As with the inner walls of the heater unit, the wall 208 of inner sleeve may be thinner than the outer sleeve 210 of the casing to improve heat transfer to the scope 210. The outer sleeve of the casing unit includes a door 212 on a flexible hinge 214 to entirely enclose the heater unit once installed.

The casing would be provided in a sterile package that would be opened immediately prior to use. FIG. 3 illustrates how the heater 102, casing 202 and scope 219 cooperate during use. Note that in context herein, "scope" should be taken to include an endoscope, laparoscope, or any other instrument having distal optics subject to fogging. As shown in FIG. 3, once the scope is inserted, door 212 is closed to maintain sterility. Button 120 is activated before or after the heater is installed in the sleeve depending upon the type of button provided.

Figure 4:
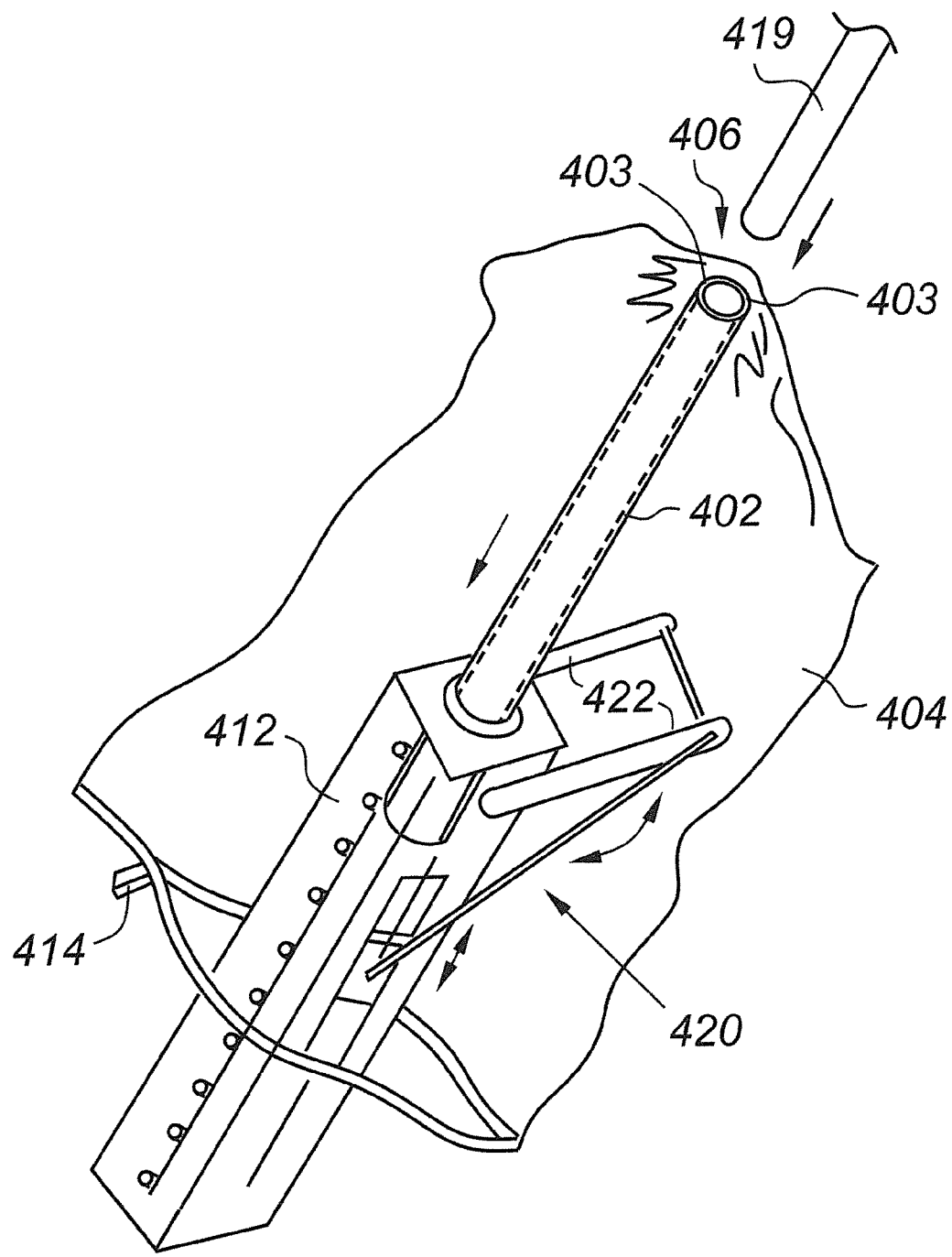
FIG. 4 is a drawing that shows various modifications that may be used with any of the embodiments disclosed herein.

FIG. 4 is a drawing that shows various modifications that may be used with any of the embodiments disclosed herein. In particular, instead of a rigid or semi-rigid outer sleeve 210, the rim 403 of inner sleeve 402 may be bonded to a flexible enclosure such as plastic bag 404. Thus, in this embodiment, the sterile casing comprises the inner sleeve 402 and bag 404. The inner sleeve 402 is bonded such that a hole 406 is provided to receive viewing instrument 419. Similar to other embodiments, however, once the heater is received within the bag 404, it is sealed, in this case with a slide lock 414. Again, although the heater unit 412 is kept out of the sterile field and reusable, the instrument 419 may nevertheless be inserted into open end of inner sleeve 402 and warmed while within the cavity of the heater.

Note further that the cross section of the heater 412 unit need not be round, in that square and other shapes may be used to prevent rolling on flat surfaces. The heater unit may also include an option mechanism 420 with adjustable support arms 422 enabling the heater to be positioned at a desired angle for use. With rechargeable batteries, the heater of FIG. 4 would nevertheless be rechargeable with a stand (not shown) including cooperating contacts or inductive apparatus.

The invention claimed is:

1. Apparatus for warming an endoscope or laparoscope having a shaft with a distal optical element susceptible to fogging, the apparatus comprising:
   an elongated heater unit having an elongated outer wall and an elongated inner cavity and a heating element to heat the cavity;
   a battery within the heater unit operative to power the heating element; and
   a sterile, disposable casing including an elongated inner sleeve with a closed end configured to be received within the elongated inner cavity of the heater unit, the casing further including an elongated outer sleeve configured to cover the outer wall of the heater unit, the elongated outer sleeve including an opening to receive the heater unit, and a closure to seal the opening such that the heater unit is contained entirely within the sterile, disposable casing when the closure is sealed, thereby enabling an endoscope or laparoscope to be inserted into an open end of the outer sleeve to be warmed by the heater unit while preventing the heater unit from entering a sterile field.

2. The apparatus of claim 1, wherein the closure is a door that closes off the opening when the heater unit is received within the casing.

3. The apparatus of claim 1, wherein the outer sleeve of the casing is a flexible bag, and wherein the closure is a sliding seal that closes off the opening when the heater unit is received within the casing.

4. The apparatus of claim 1, wherein the heating element is a heating coil surrounding the cavity of the heater unit.

5. The apparatus of claim 1, further including a charging base to receive the heater unit to recharge the battery therein.

6. The apparatus of claim 5, wherein the heater and the charging base both include a plurality of cooperating electrical contacts to recharge the battery.

7. The apparatus of claim 5, including an inductive coupling between the charging base and the heater unit to recharge the battery.

8. The apparatus of claim 1, wherein the heater unit includes a touch-sensitive switch to activate the heating element.

9. The apparatus of claim 1, wherein the heater unit includes a non-round outer cross section to prevent rolling of the heater unit.

10. The apparatus of claim 1, wherein the heater unit includes an adjustable support to position the heater unit at a desired angle during use.

11. The apparatus of claim 1, wherein the casing is provided as a sterilized unit in a protective package that is opened for use.

* * * * *